US006815423B1

(12) United States Patent
Desjardins et al.

(10) Patent No.: US 6,815,423 B1
(45) Date of Patent: Nov. 9, 2004

(54) FLUORESCENT SUBSTANCE P

(75) Inventors: Clarissa Desjardins, Quebec (CA);
Jacek Slon-Usakievicz, Quebec (CA);
Alain Beaudet, Quebec (CA)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 09/285,387

(22) Filed: Apr. 2, 1999

Related U.S. Application Data

(63) Continuation-in-part of application No. 08/682,810, filed on Jul. 10, 1996, now Pat. No. 6,054,557, which is a continuation-in-part of application No. 08/504,856, filed on Jul. 20, 1995, now abandoned.

(51) Int. Cl.$^7$ .............................................. A61K 38/00
(52) U.S. Cl. ........................... 514/15; 530/327; 435/7.1
(58) Field of Search ........................... 514/15; 530/327; 435/7.1

(56) References Cited

U.S. PATENT DOCUMENTS

| | | | | |
|---|---|---|---|---|
| 4,046,633 A | 9/1977 | Keutel | ................. | 195/103.5 R |
| 5,248,782 A | 9/1993 | Haugland | .................... | 548/110 |
| 5,274,113 A | 12/1993 | Kang et al. | .................. | 548/405 |
| 5,693,679 A | 12/1997 | Vincent et al. | ............. | 530/311 |
| 5,760,188 A | 6/1998 | Beaudet et al. | ............. | 530/402 |

FOREIGN PATENT DOCUMENTS

| | | |
|---|---|---|
| DE | 27 02 699 A1 | 12/1977 |
| DE | 3912046 A1 | 3/1990 |
| EP | 0 007 407 | 2/1980 |
| EP | 0 240 914 A2 | 10/1987 |
| EP | 0 333 071 A3 | 11/1988 |
| EP | 0 331 126 A2 | 9/1989 |
| EP | 0 466 565 A1 | 1/1992 |
| EP | 0 606 804 | 7/1994 |
| EP | 0 608 987 | 8/1994 |
| GB | 2 291 708 A | 1/1996 |
| JP | 63051400 | 3/1988 |
| WO | WO 93/04194 | 3/1993 |
| WO | WO 93/18068 | 9/1993 |
| WO | WO 95/22341 | 8/1995 |
| WO | WO 96/31531 | 10/1996 |
| WO | WO 97/04311 | 2/1997 |

OTHER PUBLICATIONS

Tota et al., "Interaction of [fluorescein–Trp$^{25}$]Glucagon With the Human Glucagon Receptor Expressed In *Drosophila* Schneider 2 Cells" *J. Biol. Chem.*, 270:26466–26472 (1995).
Varga et al., "Association Of Cell Surface Receptors For Melanotropin With the Golgi Region In Mouse Melanoma Cells", *Proc. Nat. Acad. Sci. USA*, 73:559–562 (1976).

Vrontakis et al., "Isolation and Characterization Of A Complementary DNA (Galanin) Clone From Estrogen–induced Pituitary Tumor Messenger RNA" *Journal of Biological Chemistry*, 262:16755–16758 (1987).
Walker et al., "High level Expression Of Human Neuropeptide Y Receptors In Mammalian Cells Infected With A Recombinant Vaccinia Virus" *Molecular and Cellular Endocrinology*, 91:107–112 (1993).
Yamada et al., "Cloning and Functional Characterization of a Family of Human and Mouse Somatostatin Receptors Expressed in Brain, Gastrointestinal Tract, and Kidney" *Proc. Nat. Acad. Sci.*, 89:251–255 (1992).
Yanagisawa et al., "A Novel Potent Vasoconstrictor Peptide Produced By Vascular Endothelial Cells" *Nature*, 332:411–415 (1988).
Zhao, "Attachment Of A Single Fluorescent Label To Peptides For Determination By Capillary Zone Electrophoresis" *Journal of Chromatography*, 608:239–242 (1992).
Zhuo et al., "Localization and Properties of Angiotensin II Receptors In Rat Kidney" *Kidney International*, 44:S40–S46 (1993).
Sack et al., "Cell Type–specific Binding of *Ricinus* Lectin To Nurine Cerebellar Cell Surfaces In Vitro" *Cell Tissue Research*, 228:183–204 (1983).
Sadoul et al., "Characterization And Visualization Of Neurotensin Binding To Receptor Sites In Human Brain" *Biochem. and Biophys. Res. Comm.*, 120:206–213 (1984).
Schaffer et al., "Fluorescence–activated Cell Sorting Of Embryonic Mouse and Rat Motoneurons and Their Long–term Survival In Vitro" *J. of Neuroscience*, 7:3088–3104 (1987).
Scicchitano et al., "Distribution Of Somatotatin Receptors On Murine spleen And Peyer's Patch T and B Lymphocytes" *Brain, Behavior, and Immunity*, 1:173–184 (1987).
Shecter et al., "Fluorescent Labeling of Hormone Receptors In Viable Cells: Preparation And Properties Of Highly Fluorescent Derivatives of Epidermal Growth Factor and Insulin" *Proc. Nat'l. Acad. Sci. USA*, 75:2135–2139 (1978).
Sigma Immuno Chemicals Company, FluoroTag FITC Conjugation Kit (1994).

(List continued on next page.)

*Primary Examiner*—Marianne C. Seidel
*Assistant Examiner*—C. Delacroix-Muirheid
(74) *Attorney, Agent, or Firm*—Iandiorio & Teska

(57) ABSTRACT

Light emitting compounds of the formula:

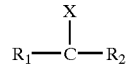

wherein $R_1$ is a light-emitting moiety and $R_2$ is a substance P-based peptide, fragment, derivative or analog thereof, said peptide being linked at an amino acid position to (C—X), wherein (C—X) is selected from the group consisting of C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties, wherein said compound exhibits substantial biological activity in the presence of a receptor having affinity for substance P-based peptides.

16 Claims, 2 Drawing Sheets

OTHER PUBLICATIONS

Song et al., "Mapping Of Angiotensin II Receptor Subtype Heterogeneity In Rat Brain" *Journal of Comparative Neurology*, 316:467–484 (1992).

St. John et al., "Analysis and Isolation of Embryonic Mammalian Neurons By Fluorescence–Activated Cell Sorting" *Journal of Neuroscience*, 6:1492–1512 (1986).

Steinkamp, "Flow Cytiometry" *Rev. Sci Instrum.* 55:1375–1400 (1984).

Tanaka et al., "Structure And Functional Expression of the Cloned Rat Neurotensin Receptor" *Neuron*, 4:947–854 (1990).

Taylor and Wang, "Fluorescently Labelled Molecules As Probes of the Structure And Function Of Living Cells" *Nature*, 284:405–410 (1980).

Tota et al., "Characterization of a Fluorescent Substance P Analog" *Biochemistry*, 33:13079–13086 (1994).

Hazum et al., "Fluorescent And Photo–affinity Enkephalin Derivatives: Preparation And Interaction With Opiate Receptors" *Biochemical And Biophysical Research Communications*, 88:841–846 (1979).

Jans et al., "Lateral Mobility of the Phospholipase C–activating Vasopressin $V_1$–type Receptor In A7r5 Smooth Muscle Cells: A Comparison With the Adenylate Cyclase–coupled $V_2$–Receptor" *EMBO Journal*, 9:2693–2699, (1990).

Kitabgi et al., (eds), *Annals NY Acad. Sci.*, 668:Table of Contents.

Kohzuki et al., "Localization And Characterization of Endothelin Receptor Binding Sites In the Rat Brain Visualized By In Vitro Autoradiography" *Neuroscience*, 42:245–260 (1991).

Maxfield, "Fluorescent Analogs Of Peptides And Hormones" *Methods in Cell Biology*, 29:13–28 (1989).

Melander et al., $^{125}$I–Galanin Binding Sites In the Rat Central Nervous System *Handbook of Chemical Neuroanatomy*, vol. II, Elsevier Publishers (1992).

Merchenthaler et al., "Anatomy And Physiology of Central Galanin–containing Pathways" *Prog. Neurobiol.*, 40:711–769 (1993).

Nawa et al., "Nucleotide Sequences of Cloned cDNAs For Two Types of Bovine Brain Substance P Prescursor" *Nature*, 306:32–36 (1983).

Niedel et al., "Receptor–mediated Internalization of Fluorescent Chemotactic Peptide By Human Neutrophils" *Science*, 205: 1412–1414 (1979).

Rivier, et al., "D–Trp$^8$–somatostatin: An Analog Of Somatostatin More Potent Than the Native Molecule" *Biochemical and Biophysical Research Communications*, 65:746–751 (1975).

Roettger, et al., "Insulation Of A G Protein–coupled Receptor On the Plasmalemmal Surface Of the Pancreatic Acinar Cell" *J. Cell Biol.*, 130: 579–590 (1995).

Rubanyi et al., "Endothelins: Molecular Biology, Biochemistry, Pharmacology, Physiology, And Pathophysiology" *Pharmacological Reviews*, 46:325–415 (1994).

Christophe, "Type I Receptors For PACAP (A Neuropeptide Even More Important Than VIP?)" *Biochimica et Biophysica Acta*, 1154:183–199 (1993).

Cushman, "Spectrophotometric Assay And Properties Of the Angiotensin–converting Enzyme of Rabbit Lung" *Biochemical Pharmacology*, 20:1637–1648 (1971).

Epelbaum, "Somatostatin Receptors In the Central Nervous System" *Basic and Chemical Aspects of Neuroscience*, 4:17–28 (1992).

Faure et al., "Binding and Internalization of Neurotensin In Hybrid Cells Derived From Septal Cholinergic Neurons" *Annals of the New York Academy of Sciences*, 668:345–347 (1992).

Faure et al., "Synthesis of a Biologically Active Fluorescent Probe For Labeling Neurotensin Receptors" *The Journal of Histochemistry and Cytochemistry*, 42:755–763 (1994).

Garland et al., "Agonist–induced Internalization Of the Substance p ($NK_1$) Receptor Expressed in Epithelia Cells" *Biochem. J.*, 303:177–186 (1994).

Grady et al., "Delineation of the Endocytic Pathway of Substance P and Its Seven–Transmembrane Domains NK1 Receptor" *Molecular Biology of the Cell*, 6:509–524 (1995).

Goldstein et al., "DAKLI: A Multipurpose Ligand With High Affinity And Selectivity For Dynorphin (kappa opioid) Binding Sites" *Proc. Nat'l Acad. Sci.*, 85:7375–7379 (1988).

Guillon et al., "Lateral Mobility of the Phospholipase C–activating Vasopressin $V_1$–type Receptor In A7r5 Smooth Muscle Cells: A Comparison With the Adenylate Cyclase–Coupled $V_2$–receptor" *Peptides*, 13:7–11 (1992).

Haigler et al., "Visualization By Fluorescence of the Binding and Internalization of Epidermal Growth Factor In Human Carcinoma Cells A–431" *Proc Natl Acad Sci USA*, 75:3317–3321 (1978).

Haugland et al., *Noninvasive Techniques In Cell Biology*, Wiley–Liss, Inc. (1990).

Haugland, *Handbook of Fluorescent Probes and Research Chemicals*—5$^{th}$ edition (1992).

Hazum et al., "Cluster Formation of Opiate (enkephalin) Receptors In Neuroblastoma Cells: Differences Between Agonists And Antagonists And Possible Relationships To Biological Functions" *Proc. Nat'l Acad. Sci.*, 77:3038–3041 (1980).

Amoscato et al., "Synthesis of Two Biologically Active Fluorescent Probes of Thymopentin" *Peptide Protein Res.*, 29:177–186 (1987).

Ashworth et al., "Visualization of the Thyropoin–releasing Hormone Receptor And Its Ligand During Endocytosis And Recycling" *Proc. Nat'l. Acad. Sci. USA*, 92:512–516 (1995).

Beaudet et al., "Internalization And Intracellular Mobilization Of Neurotensin In Neuronal Cells" *Biochemical Pharmacology*, 47:43–52 (1994).

Bowden et al., "Direct Observation of Substance P–induced Internalization of Neurokinin 1 ($NK_1$) Receptors at Sites of Inflammation" *Proc. Nat'l. Acad. Sci. USA*, 91:8964–8968 (1994).

Bunnett et al., "Characterization Of Receptors Using Cyanine 3–labeled Neuropeptides" *Peptides*, 16:733–740, (1995).

Cardullo et al., "Speract Receptors Are Localized on Sea Urchin Sperm Flagella Using a Fluorescent Peptide Analog" *Developmental Biology*, 162:600–607 (1994).

Carraway et al., "The Isolation of a New Hypotensive Peptide, Neurotensin, From Bovine Hypothalami" *J. of Biological Chemistry*, 248:6854–6861 (1973).

Cauvin et al., "Properties and Distribution of Receptors For Pituitary Adenylate Cyclase Activating Peptide (PACAP) In Rat and Spinal Cord" *Regulatory Peptides*, 35:161–173 (1991).

Chard, Laboratory Techniques in Biochemistry and Molecular Biology, Elzevier Biomedical Press, New York.

Cheng et al., "Fluorescent Rhodamine–Labeled Thyroid Hormone Derivatives" *FEBS Letters*, 100:113–116 (1979).

Cheng et al., "Receptor–mediated Uptake Of 3,3'5–triiodo–L–thyronine By Cultured Fibroblasts" *Proc. Nat'l. Acad. Sci. USA*, 77:3425–3429 (1980).

Chersi et al., "Preparation And Utilization Of Fluorescent Synthetic Peptides" *Biochemica et Biophysica Acta*, 1034:333–336 (1990).

FLUORESCENT SUBSTANCE P

CROSS REFERENCE TO RELATED APPLICATIONS

This application is a continuation-in-part application of U.S. Ser. No. 08/682,810 filed Jul. 10, 1996 and entitled "Fluorescent Peptides", now U.S. Pat. No. 6,054,557 which is a continuation-in-part application of U.S. Ser. No. 08/504,856, having the same name and filed Jul. 20, 1995 now abandoned.

BACKGROUND OF THE INVENTION

This invention relates to peptide-based compounds having light-emitting moieties. Peptides may be chemically linked with detectable "labels" and used, for example, to monitor peptide, cytokine, drug, and hormone receptors at the cellular level. Typically, the labeled peptide is placed in contact with a tissue or cell culture where it binds to an available receptor. Once bound, the label is detected, allowing properties such as receptor distribution or receptor binding kinetics to be monitored.

Peptides are typically labeled with radioactive elements such as $^{125}$I or $^3$H. In this case, emission of high-energy radioactive particles is monitored using standard γ-ray detectors, thereby allowing detection of the label. While detection techniques for $^{125}$I and $^3$H are well-known, radioactive compounds by nature have limited half lives, and are often both toxic and expensive. Moreover, current detection technology makes it difficult or impossible to detect radioactive probes in real-time, thereby precluding study of kinetic processes.

Substance P is a particularly desirable peptide to label and use to monitor cell receptors, as this compound exhibits multiple biological roles including stimulation of visceral smooth muscle in the intestine and uterus. Substance P is an eleven amino acid peptide, first isolated in the brain and intestine, and has been identified as a major afferent neurotransmitter in pain transmission in the spinal chord (Kuraishi et al, *Neuroscience* 30:241 (1989)). Substance P is responsible for the release of endogenous substances, including the release of histimine from mast cells (Regoli et al. *Pharmacological Reviews* 46(4):551 (1994)).

SUMMARY OF THE INVENTION

The present invention provides a compound containing a substance P peptide and a light-emitting moiety that is both biologically active and optically detectable. The peptide is chemically attached to the light-emitting moiety at an amino acid position that is not involved in binding to the peptide receptor. In this way, the peptide's affinity for the binding site is not significantly decreased, and the compound retains high biological activity and can be easily detected using standard optical means.

In general, in one aspect, the invention provides a biologically active compound of the formula:

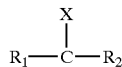

where $R_1$ is a light-emitting moiety and $R_2$ is a substance P-based peptide and fragment, derivative or analog thereof. The peptide is linked at a first amino acid position to (C—X) which, in turn, is selected from the group including C=O, C=S, CH(OH), C=C=O, C=NH, CH$_2$, CH(OR), CH(NR), CH(R), CR$_3$R$_4$, and C(OR$_3$)OR$_4$ where R, R$_3$, and R$_4$ are alkyl moieties or substituted alkyl moieties. Preferably, the compound exhibits substantial biological activity in the presence of receptors having affinities for substance P-based peptides. The compound may also be in the form of a pharmaceutically acceptable salt or complex thereof. Preferably, the first amino acid position bound to (C—X) is included in the N-terminus amino acid of the substance P-based peptide.

In other preferred embodiments, the substance P-based peptide includes the amino acid sequence Arg-Pro-Lys-Pro-Gln-Gln-Phe-Phe-Gly-Leu-Met (SEQ ID NO:1) and the Arg-residue is attached to the (C—X) moiety. The arginine residue preferably is chemically bound to the (C—X) moiety through the N-terminus amine group. In still other preferred embodiments, the (C—X) bond is either C=O or C=S. In another preferred embodiment, the peptide may be amidated at the C-terminus.

In other preferred embodiments, the light-emitting moiety ($R_1$) is selected from the group including 4,4-difluoro-4-bora-3a-diaza-s-indacene, fluorescein, FTC, Texas red, phycoerythrin, rhodamine, carboxytetramethylrhodamine, 4'6-diamidino-2-phenylindole (DAPI), indopyras dyes, Cascade blue, coumarins, nitrobenzo-2-oxa-diazole (NBD), Lucifer Yellow, propidium iodide, CY3, CY5, CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lys) in the presence of a nucleophile (i.e. CN$^-$) to form fluorescent isoindoles, dansyl dyes fluorescamine and dabcyl chloride, 5-((((2-iodoacetyl)amino)ethyl)amino)naphthalene-1-sulfonic acid, long lifetime dyes comprised of metal-ligand complexes (MLC) which consist of a metal center (Ru, Re, Os) and organic or inorganic ligands complexed to the metal such as [Ru(bpy)3]$^{2+}$ and [Ru(bpy)$_2$(dcbpy)], and the like and derivatives thereof. The light-emitting moiety can be attached to the peptide by reaction of a reactive side group (of the light-emitting moiety) with the N-terminus amino acid of substance P. Suitable linking moieties include, by way of example only, indoacetamide, maleimide, isothiocyanate, succinimidyl ester, sulfonyl halide, aldehydes, glyoxal, hydrazine and derivatives thereof.

By "substance P-based compound" is meant a peptide which includes substance P, fragments of substance P, derivatives or analogs thereof. Substance P-based peptides may be peptides whose sequences differ from substance P's wild-type sequence by only conservative amino acid substitutions. For example, one amino acid may be substituted for another with similar characteristics (e.g., valine for glycine, arginine for lysine, etc.) or by one or more non-conservative amino acid substitutions, deletions, or insertions which do not abolish the peptide's biological activity. Other useful modifications include those which increase substance P's stability. The peptide may contain, for example, one or more non-peptide bonds (which replace a corresponding peptide bond) or D-amino acids in the peptide sequence. Additionally, the C-terminus carboxylic acid group may be modified to increase peptide stability. For example, as described above, the C-terminus may be amidated or otherwise derivatized to reduce the peptide susceptibility to degradation.

In all cases, by "substantially biologically active" is meant the compound binds to a receptor having an affinity IC50 value for the compound which is no more than 15 times, more preferably no more than 10 times and most preferably equal to or less than that of the corresponding unlabeled peptide. Receptor affinity in this case can be determined using known methods, such as methods involving competitive binding of radioactively labeled peptides or by using known methods of fluorescence polarization or other known fluorescence technique for measuring the $K_d$ for the receptor/peptide interaction.

By "low" or "no" biological activity or "biologically inactive" is meant biological activities less than 1.0% of the biological activity of $R_2$—H in the presence of a receptor having affinity for substance P.

The above-identified compound is useful in the labeling of cell receptor sites, cell sorting, flow cytometry and performing fluoroimmunoassays. In another aspect, the invention provides a method for labeling a receptor having an affinity for a substance P-based peptide by contacting the receptor with one or more of the compounds described above. Cell receptor sites, can be imaged by contacting candidate cell receptor sites with the compound of the invention, and then detecting the bound compounds as an indication of the cell receptor sites. Cell sorting can be performed by contacting a population of cells with compound and isolating cells bound to the compound. Flow cytometry can be performed by contacting a population of cells with the compound and detecting cells bearing receptors on their surfaces by detecting cells bound to the compound.

The invention has many advantages. In a general sense, peptide-containing compounds which retain their biological activity after being labeled with light-emitting moieties have a wide variety of biological applications. Such compounds can be used to identify, visualize, quantify, target and select receptors on cells and tissues both in vitro and in vivo. These compounds may be used in place of more conventional labeled peptides, such a $^{125}I$ radiolabeled peptides. Radiolabeled compounds are often toxic, environmentally hazardous, chemically unstable and have, by the nature of the radioactive decay rate, relatively short lifetimes. In contrast, fluorescently-labeled substance P is relatively safe and non-toxic, thereby allowing it to be synthesized and used without employing special laboratory procedures. Similarly, following use, fluorescent substance P may be easily disposed, whereas disposal of radioactive compounds is both time-consuming and costly. In addition, fluorescent markers for substance P receptors are stable. and may be stored for extensive periods of time without undergoing extensive degradation.

Use of substance P in the labeled compound is also advantageous. As described above, substance P exhibits biological activity in organs such as intestine and uterus, and is involved in pain transmission in the spinal cord and in the release of histimines in mast cells, and can therefore be used as a probe to investigate a large number of different cell types. In addition, this peptide has a relatively simple structure (11 amino acids) and can be synthesized and isolated with standard, well-known techniques.

During typical experiments, fluorescent markers for substance P receptors emit optical signals, and thus may be monitored by eye or with the aid of external optical detectors. In this way, the fluorescent peptides obviate the need for secondary detection steps sometimes used for radiolabeled compounds or incubation with secondary labeled compounds. Detection of optical radiation is, in general, relatively simple and cost-effective compared to detection of radioactive particles (e.g., α-particles); conventional charge-coupled device (CCDs) or light-sensitive cameras can therefore be used without modification for this application.

In addition, because of their high optical emission rates and well-characterized emission cross sections, fluorescent markers attached to substance P receptors can be used for real-time, quantified imaging of a number of dynamic biological phenomena, such as kinetics associated with receptor binding. The compounds can also be used for static processes, such as monitoring peptide distribution within a cell. Substance P receptors marked with fluorescent peptides may also be used in flow cytometry, confocal microscopy, fluorescence polarization spectroscopy, and any other techniques exploiting the optical detection of fluorescence or photoluminescence.

Other advantages and features of the invention will become apparent from the following detailed description, and from the claims.

DETAILED DESCRIPTION OF THE INVENTION

Figure 1:
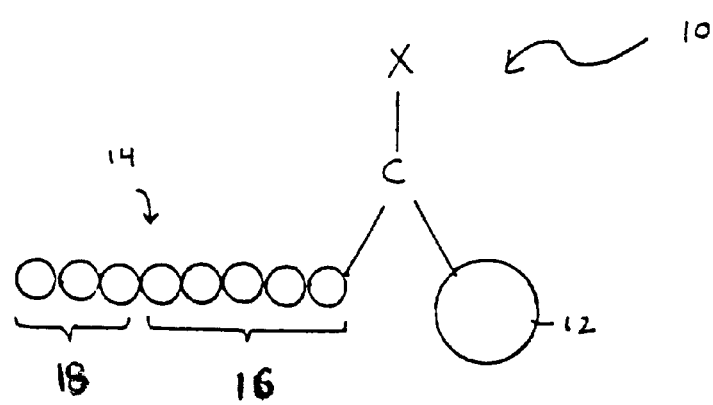
FIG. 1 is a schematic drawing of the chemical structure of fluorescently-labeled peptide according to the invention.

Referring first to FIG. 1, in a preferred embodiment, a fluorescent peptide 10 according to the invention includes a light-emitting moiety 12, such as a fluorescent dye, linked via a (CX) bond to a peptide moiety 14. The peptide moiety 14 includes amino acid residues of the substance P peptide, and fragments, derivatives or analogs thereof. Region 18 is presumed to be involved in the biological activity of the peptide complex.

In order to retain substantial biological activity and affinity for substance P receptors, the peptide is attached to the (CX) linking moiety at an amino acid residue which is in a region 16 which is not biologically active, i.e., it is not significantly involved in the peptide's biological role. In this manner, the light-emitting moiety does not sterically hinder or otherwise significantly affect the region involved in receptor binding and the biological activity of the compound is thus maintained. For example, in a preferred embodiment, the peptide moiety is attached via an αN-Arg1 bond to the light emitting moiety through a (C=O) bond. The light-emitting moiety may be covalently bonded to the (CX) linking group at any available position. The (CX) linking group represents the bond formed between the light-emitting moiety and the peptide upon reaction and this bond may include groups such as C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties.

Fluorescent peptides of this type have amino acids which are available for binding to substance P-recognizing receptors, thereby enabling the peptide to be used for labeling purposes. Once bound to an available receptor, the attached light-emitting moiety retains optical properties similar to those of the unbound light-emitting molecule. In this way, the fluorescent peptide can bind to the corresponding receptor and emit light following absorption of an incident optical field, and thus serve as a marker for the substance P receptor. This allows the receptor to be "labeled" and permits investigation, for example, of peptide/receptor interactions. In particular, labeled peptides participating in receptor/peptide interactions can be monitored to determine the location of receptors in cell or tissue samples, and additionally allow quantification of receptors, determination of the receptor affinity for various ligands, or the identification of various populations of cells.

Substance P-based peptides may be synthesized using techniques known in the art, extracted from natural systems, or obtained from commercial sources (e.g., American Peptide, Peninsula, Neosystems, Sigma, BASF). A list of substance P analogs which may be used to practice the invention may be obtained from American Peptide Co., Inc product catalogue. Typically, the peptide is either purchased or synthesized using conventional solid-phase synthetic techniques. Preferably, the peptide is substantially pure, meaning that it is at least 60% by weight free from the other compounds with which it is naturally associated.

In general, any dye, porphyrin, fluorophore, or other light-emitting compound may be complexed with the substance P-based peptide. In preferred embodiments, the light-emitting moiety is selected from the group including 4,4-difluoro-4-bora-3a-diaza-s-indacene, fluorescein, FTC, Texas red, phycoerythrin, rhodamine, carboxytetramethylrhodamine, DAPI, indopyras dyes, Cascade blue, coumarins, NBD, Lucifer Yellow, propidium iodide, CY3, CY5, CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lysine) in the presence of a nucleophile (i.e. $CN^-$) to form fluorescent isoindoles, dansyl dyes fluorescamine and dabcyl chloride, 5-((((2-iodoacetyl)amino)ethyl)amino)naphthalene-1-sulfonic acid, long lifetime dyes comprised of metal-ligand complexes (MLC) which consist of a metal center (Ru, Re, Os) and organic or inorganic ligands complexed to the metal such as $[Ru(bpy)_3]^{2+}$ and $[Ru(bpy)_2(dcbpy)]$, and the like and derivatives thereof. The synthesis and structures of several dyes which may be used are described in U.S. Pat. Nos. 5,248,782; 5,274,113; and 5,187,288, the contents of which are incorporated herein by reference. Other light-emitting moieties used in labeling or other applications may be attached to the peptide. For example, suitable light-emitting moieties are described in "Handbook of Fluorescent Probes and Research Chemicals—5th Edition" by Richard P. Haugland, 1994; and "Design and Application of Indicator Dyes", *Noninvasive Techniques in Cell Biology:* 1–20 by Richard P Haugland et al., Wiley-Liss Inc. (1990), the contents of each of which is incorporated herein by reference.

Once the desired peptide is obtained, fluorescent peptides having high biological activities are made by attaching the light-emitting moiety to the first amino acid position of the substance P-based moiety. In general, this reaction is carried out by modifying a functional group on the peptide, most typically a thiol or amine group, so that this moiety may be easily attached to the light-emitting compound. Reactions for such modifications are described in, for example, "*Handbook of Fluorescent Probes and Research Chemicals—5th Edition*" (supra). In general, thiols react with alkylating groups (R'—Z) to yield relatively stable thiol ethers (R'—S—R), e.g., (C—X) is the α-carbon of R', with the leaving group Z preferably being a halogen (e.g., Cl, $Br^-$, I) and the like. In particular, the most common reagents for derivatization of thiols are haloacetyl derivatives. Reaction of these reagents with thiols proceeds rapidly at or below room temperature in the physiological pH range.

The conditions used to modify amine moieties of the desired peptide will depend on the class of amine (e.g., aromatic, aliphatic) and its basicity. Aliphatic amines, such as the α-amino acid groups of lysine and arginine, are moderately basic and reactive with acylating reagents. The concentrations of the free base form of the aliphatic amines below pH 8 is very low; thus, the kinetics of acylation reaction of amines by isothiocyanates, succinimidyl esters, and other reagents is strongly pH-dependent. Although amine acylation reactions should usually be carried out above pH 8.5, the acylation reagents degrade in the presence of water, with the rate increasing as the pH increases. Therefore, a pH of 8.5–9.5 is usually optimal.

In general, reactive groups on the light-emitting moiety, such as unsaturated alkyl groups or acylating moieties, will react with the modified peptide to form a dye/peptide bond. The chemical structure of the light-emitting moiety may affect the synthetic route used to synthesize the fluorescent substance P analog. It may be necessary, for example, to modify the light-emitting moiety so that it includes a reactive group prior to exposing this moiety to the desired peptide. Such side groups may include indoacetamide, maleimide, isothiocyanate, succinimidyl ester, sulfonyl halide, aldehyde, glyoxal, and hydrazine derivatives. Amino acids including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine may be labeled according to the method described herein.

The chemistry used to synthesize the fluorescent peptide is not greatly dependent upon the exact structure of the substance P analog. Thus, the general procedure outline below may be used for most substance P-based peptides. Attachment of this peptide to a light-emitting moiety is described in detail in the Examples provided below.

Once synthesized, the resulting complex is purified, preferably using a column method such as high pressure liquid chromatography (HPLC), and then eluted. Collected fractions are then screened using analytical methods to determine if adequate biological activity is present. Fluorescent substance P analogs having adequate biological activities are selected by first exposing these analogs to substance P receptors; compounds binding effectively to these sites are then isolated from relatively inactive fluorescent peptides. In general, this selection process can be performed using standard techniques, such a column chromatography or other analytical techniques known in the art. The selection process is designed to allow maintenance of the compound's pharmacological binding, and thus allows only the dye/peptide compounds exhibiting substantial biological activities to be separated from relatively inactive compounds.

Figure 2:
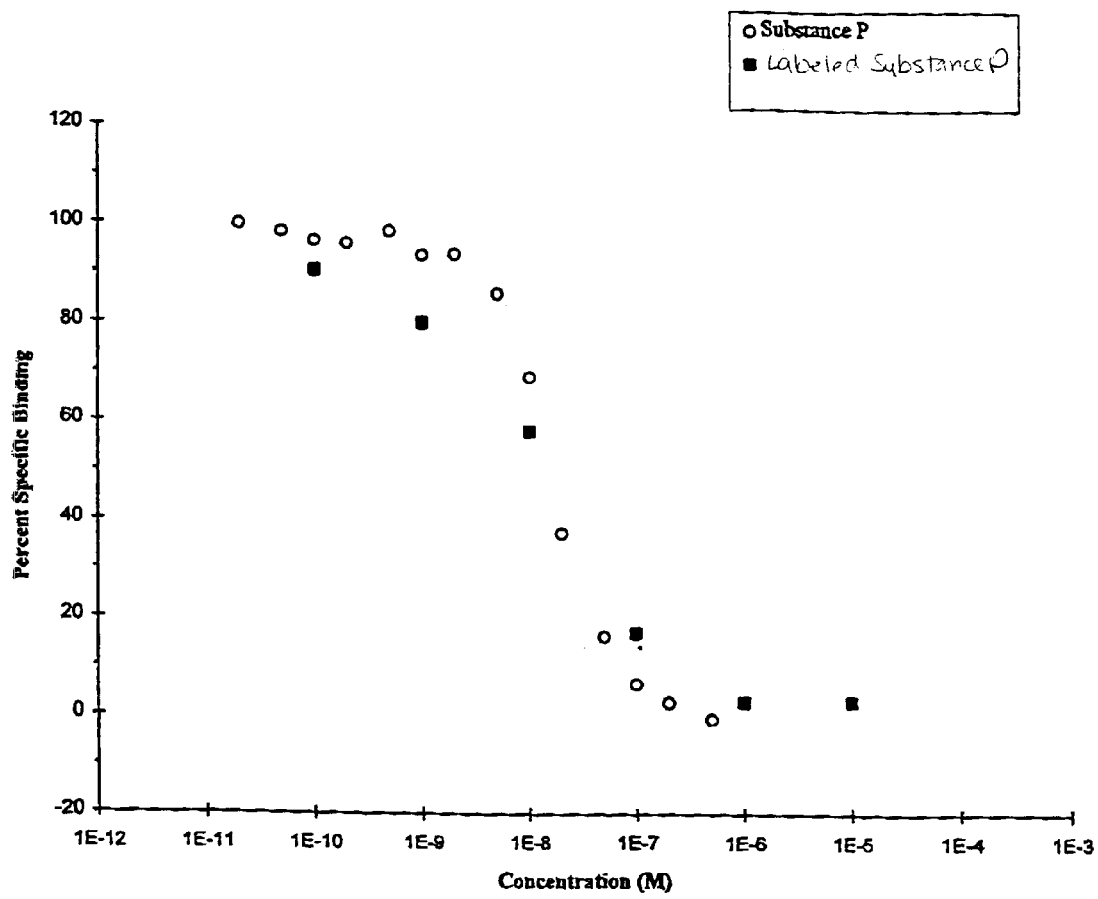
FIG. 2 is an IC50 curve showing displacement of $^{125}I$ labeled substance P by increasing concentration of unlabeled and fluorescently labeled substance P.

Referring now to FIG. 2, a fluoresceinyl-substance P with the amino acid sequence Arg-Pro-Lys-Pro-Gln-Gln-Phe-Phe-Gly-Leu-Met-$NH_2$ was tested to determine its affinity for substance P receptor sites. The fluoresceinyl-substance P compound absorbs light in the range of 494 nm and features an emission spectrum centered around 518 nm. The compound exhibits comparable, dose-dependent binding to substance P receptors when compared to native substance P peptides, as determined by displacement of radiolabeled-substance P bound to rat submaxillary gland membranes. The concentrations at which 50% of the binding is inhibited (i.e., the IC50) is 10 nM for the fluorescein-labeled compound, as compared to 16 nM for the unlabeled substance P. The $IC_{50}$ is related to the binding constant $K_i$ by the formula $IC_{50}=K_i(1+F_L/K_d)$, where $F_1$ is the concentration of the free labeled ligand and $K_d$ is the dissociation constant for the labeled ligand. The $K_i$ for this compound was 22.1 nM for the labeled compound versus 8.6 nM for the unlabeled compound. This demonstrates the high degree of retention of biological activity.

In cases where it is not known which amino acid site may be complexed to form the fluorescent peptide of the invention, the peptide-fluorophore complexes may be screened to identify suitable complexes. The general synthetic method for identifying light-emitting biologically active compounds of the invention is as follows.

The substance P-based peptide and the fluorophore of choice are incubated to form a mixture of compounds. Incubation is performed under conditions which permit optimal peptide labeling. Typically, a solution containing the peptide at a concentration of about $10^{-2}$–$10^{-4}$ M is mixed with the light-emitting moiety in a highly basic solution, i.e., pH 9.3–10.7 such as a carbonate buffer, in at least a 1:4 peptide:light-emitting moiety molar ratio. The solution is mixed at room temperature for a time of between about 24–48 hours, and is protected from light and shaken periodically. The resulting mixture includes biologically active and inactive whole peptides, cleaved fragments of peptides and singly and multiply labeled peptides.

After covalent bonding of the light-emitting moiety and the peptide occurs, unbound fluorophore is removed. In general, this step is performed using standard techniques such as column chromatography or other analytical techniques known in the art. In a typical example, unreacted amounts of the free fluorophore are removed using a G-50 column equilibrated with phosphate buffered saline (pH 7.4) and spun a 3000 rpm for a period of between 0.5 and 20 minutes. The resultant eluent contains a mixture of labeled biologically active and inactive peptides.

This solution is then collected and subjected to a high-stringency pharmacological binding assay. In this assay, only biologically active compounds are bound to tissue receptors; inactive compounds are washed away. The assay is typically performed on tissue sections, receptor-coated columns or membrane homogenates. In a typical example, an aliquot of the fluorescent peptide mixture is first dissolved in an aqueous solution (1:100) and incubated with an immobilized tissue sample containing high numbers of the peptide receptor, e.g., receptor transfected membrane homogenates.

The selection process is designed to separate compounds exhibiting substantial biological activity from those relatively inactive compounds. If necessary, during the assay, binding of the biologically active compounds may be rapidly observed visually, in a fluorometer or by using more sensitive techniques such as fluorescence polarization spectroscopy.

The receptor-bound compounds are then removed from the tissue surface and analyzed to identify the site at which the fluorophore is attached, i.e., the site allowing fluorophore attachment without interference with receptor binding. Biologically active compounds bound to membrane receptors are separated from the remaining inactive fluorescent peptides in solution, either by centrifugation of membrane homogenates (typically at 3000 rpm for about 5 minutes) or, in the case of tissue sections, by rapidly rinsing the sections in incubation buffer at 4° C. The membranes are then resuspended in binding buffer with the biologically active compound removed from the cell surfaces by incubation in a high salt/acid wash solution.

Once isolated, biologically active compounds are analyzed using known techniques, such as carboxypeptidase digestion and capillary electrophoresis, laser induced capillary zone electrophoresis, mass spectroscopy, and/or HPLC or amino acid sequencing, to identify the site of attachment between the light-emitting moiety and the peptide.

Fluorescent substance P compounds selected to have high biological activity have a number of uses. For most applications, the fluorescent compound is first contacted with the sample of interest. The compound is then incubated with the cell or tissues of the sample for a select time period and allowed to interact with the substance P receptor. If necessary, excess, non-specifically bound compound may be washed away.

Once the peptide is bound to the desired receptor site, the labeled sample is imaged using standard techniques known in the art. Conventional microscopy methods, such as fluorescence or confocal microscopy, may be used to optically excite and then detect emission from the labeled receptors. Other imaging techniques which can be used with the fluorescent substance P-based compounds include atomic force microscopy, fluorescence polarization spectroscopy, and fluorimetry.

Using the above techniques, small-scale features in the cell which normally would be difficult or impossible to detect are observed. For example, this allows visualization of intracellular receptor sites. Moreover, labeled peptides participating in peptide-receptor interactions can be monitored to determine the location of receptors, to determine receptor affinity for various unknown ligands (drug screening), and to identify various populations of cells endowed with peptide receptors. Optical radiation emitted from the fluorescing moiety can be easily and rapidly detected, allowing the fluorescent peptides to be used to monitor real-time receptor/peptide interactions. In this way, the compounds permit study of kinetic processes in the cell. Other applications include receptor sorting using FACS (fluorescence-associated cell sorting) and measurement of serum peptide levels using FIA (fluorescent immunoassays) either in vivo or in vitro for research or diagnostic purposes. In general, techniques which may utilize the compounds of the invention include, without limitation, flow cytometry, cell sorting (for example, top isolate populations of cells bearing a receptor of interest), tumor marking, competitive binding assays for drug screening, fluorescent immunoassays, and other in vitro experimental techniques involving compound labeling according to techniques known in the art.

The following Examples are used to more particularly point out the synthesis, selection methods, and use of fluorescent substance P analogs having high biological activities.

EXAMPLE 1

Synthesis of substance P peptide. Peptides were synthesized using solid phase peptide synthesis methods either manually or automated (MPS396 peptides synthesizer, Advanced ChemTech). Coupling of amino acid residues was accomplished via Fmoc peptide synthesis chemistry (Fields, et al., 1990, IJPPR 35, 161). Syntheses were performed on Wang or on amide Rink resins, with fully side chain protected of amino acids. BOP, PyBOP or TBTU were used as activation agents depending on the chemistry and difficulty of the coupling reaction. All chemicals were purchased from Advanced ChemTech, Bachem and Calbiochem/NovaBiochem. Formation of each peptide bond between residues of the sequence was ensured by using a 3 to 6 fold excess of coupling reagents and by "double coupling"; meaning that the coupling reaction was repeated for each amino acid added to the growing peptide chain.

Fluorescein Labeling of Peptides. Substance P peptide was synthesized using an orthogonal protection scheme making it possible to deprotect the N-terminal amino group of arginine #1 while leaving remaining reactive groups in the peptide protected and the peptide attached to the resin.

A 3-fold excess (estimated peptide in nM to fluorescein) of the carboxylic form of fluorescein was used and the reaction was allowed to proceed for 24 hours. The reaction was stopped by repeated washing (10×12 ml) with DMF followed by methanol (3×12 ml) and ethanol (2×12 ml). The resin was air dried prior to cleavage from the resin, as described in the procedure above.

After the synthesis the peptides were cleaved from the resin using the Reagent K as a cleavage mixture. Water (2.5%), TIS (2.5%) EDT (2.5%) were used as scavengers. The peptides were then precipitated with cold diethyl ether. The precipitates were centrifuged, washed three times with diethyl ether, dissolved in 20%–50% acetonitrile/water mixture and lyophilized. Analytical data of crude products were performed using analytical reverse phase HPLC and electrospray mass spectroscopy.

The crude peptides were purified by HPLC on a Vydac C18 or C4 column, 2.5×25 cm, using a linear gradient of 10–50% acetonitrile in water, with 0.06% trifluoroacetate (TFA) or with 0.1% triethanolamine acetate buffer pH7.8 (1%/min gradient, 10 ml/min flow rate). Monitoring by UV at 215 nm or 254 nm. Analytical HPLC was used to estimation or purity of fractions. The final products were obtained as lyophilized with at least 95% purity estimated by analytical HPLC (Vydac C18, 0.46×25 cm, linear gradient 10–60% acetonitrile in water, 0.1% TFA, 1%/min, 1 ml/min flow rate, detection by UV absorption at 215 nm and/or 254 nm. The pure peptides were identified by molecular mass analysis using a SCIEX API III mass spectrometer.

The fluorescence intensity of the labeled peptides were measured on Beacon Fluorescence Polarization System (Panavera) or Cytofluor 96 well plate reader at gain 85.2 nmols sample of peptide dissolved in 50 ul of DMSO, vortexing and aliquoted to final concentration of 1 uM with buffer EARLS (450 uL), pH 7.4. Intensity of fluorescence (Em. 450/50 nm–Ex 530/25 nm) was measure for four concentrations in the range of 10–100 nmolar. Linear regression was used for slope calculation. This value was used to calculate of percentage of fluorescence of fluorescein itself as a sensitivity of specific response.

EXAMPLE 2

Pharmacological Binding. Determination of IC50 for labeled peptides.

Samples were prepared for IC50 determination by dissolving 2–10 nmols of the sample into a final volume of 0.5 mL. In order to fully dissolve the peptide, the sample was reconstituted in 20 uL DMSO, vortexing well to ensure that all powder was completely dissolved, and then adding 0.48 mL of double distilled water. The stock solution was aliquoted to avoid repeated freezing and thawing of peptide. Unused aliquots were stored at −20° C. (protected from light) for maximum 24 hr.

Receptor binding was carried out on tissues of rat submaxillary gland membranes. Test were conducted in at least duplicate with three repeats recommended at 5–7 test concentrations (from $10^{-11}$–$10^{-6}$ M depending on the binding values).

Data for native and labeled peptides were analyzed by non-linear curve fitting. This included statistical evaluation of fit and calculation of IC50 and $K_i$ values.

Other embodiments are within the scope of the following claims.

What is claimed is:

1. A compound of the formula:

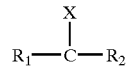

wherein $R_1$ is a light-emitting moiety and $R_2$ is a substance P-based peptide, fragment, derivative or analog thereof, wherein $R_2$ is comprised of Arg-Pro-Lys-Pro-Gln-Gln-Phe-Phe-Gly-Leu-Met (SEQ ID NO: 1), said peptide being linked at an amino acid position to (C—X), wherein (C—X) is selected from the group consisting of C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties, wherein said compound exhibits substantial biological activity in the presence of a receptor having affinity for substance P-based peptides.

2. The compound of claim 1 wherein said amino acid position comprises the N-terminus of said substance P-based peptide.

3. The compound of claim 1 wherein $R_1$ is bound, through C, to a region of said $R_2$ peptide which is not involved in said biological activity.

4. The compound of claim 1 wherein said substance P-based peptide binds to a human receptor.

5. The compound of claim 2 wherein said N-terminus amino acid residue is arginine.

6. The compound of claim 5 wherein said arginine residue of said substance P-based peptide is attached to (C—X) at αN-position.

7. The compound of claim 1 wherein said light-emitting moiety is selected from the group consisting of 4,4-difluoro-4-bora-3a-diaza-s-indacene, fluorescein, FTC, Texas red, phycoerythrin, rhodamine, carboxytetra-methylrhodamine, DAPI, indopyras dyes, Cascade blue, coumarins, NBD, Lucifer Yellow, propidium iodide, CY3, CY5, CY9, dinitrophenol (DNP), lanthanide cryptates, lanthanide chelates, non-fluorescent dialdehydes which react with primary amines to form fluorescent isoindoles, fluorescamine and dabcyl chloride, 5-((((2-iodoacetyl)amino)ethyl)amino)naphthalene-1-sulfonic acid, long lifetime dyes comprised of metal-ligand complexes (MLC) and derivatives thereof.

8. The compound of claim 1 wherein (C—X) is selected from the group consisting of C=O and C=S.

9. The compound of claim 1 wherein said compound is a pharmaceutically acceptable salt or complex thereof.

10. A method for labeling a receptor having an affinity for a substance P-based peptide by contacting said receptor with the compound of claim 1.

11. A method for generating a biologically active compound of claim 1, comprising:

reacting $R_1$ and $R_2$ in an aqueous solution to form a mixture comprising the compound of claim 1 and secondary compounds having biological activities less than 0.25% of the biological activity of $R_2$—H in the presence of a receptor having affinity for substance P;

contacting the mixture with a receptor for substance P; and isolating from said mixture a light-emitting compound exhibiting substantial biological activity in the presence of said substance P receptor.

12. The method of claim 11 wherein said isolating step comprises:

releasing said light-emitting compound from said substance P receptor; and isolating said light-emitting compound.

13. The method of claim 12 wherein said step of isolating said light-emitting compound includes selection by high pressure liquid chromatography.

14. A method for imaging cell receptor sites comprising contacting candidate cell receptor sites with a compound of claim 1 and detecting said bound compound as an indication of said cell receptor sites.

15. A method of cell sorting comprising contacting a population of candidate cells with a compound of claim 1 and isolating cells bound to said compound.

16. A method of flow cytometry comprising contacting a population of cells with a compound of claim 1 and detecting cells bearing receptors on their surfaces by detecting cells bound to said compound.

* * * * *